United States Patent
Koplin et al.

(10) Patent No.: US 8,574,520 B2
(45) Date of Patent: Nov. 5, 2013

(54) METAL OXIDE SUPPORT MATERIAL CONTAINING NANOSCALED IRON PLATINUM GROUP METAL

(75) Inventors: Tobias Joachim Koplin, Ludwigshafen (DE); Imme Domke, Mannheim (DE); Christopher R. Castellano, Ringoes, NJ (US); Gerald Stephen Koermer, Basking Ridge, NJ (US); Wolfgang Schrof, Neuleiningen (DE); Robert Feuerhake, Mannheim (DE); Gunnar Schornick, Neuleiningen (DE); Anna Cristadoro, Heppenheim (DE); Daniel Schönfelder, Brussels (BE); Hartmut Hibst, Schriesheim (DE); Mattijs Gregor Jurriaan Ten Cate, Heidelberg/Boxberg (DE)

(73) Assignee: BASF SE Ludwigshafen (DE)

(*) Notice: Subject to any disclaimer, the term of this patent is extended or adjusted under 35 U.S.C. 154(b) by 0 days.

(21) Appl. No.: 13/516,291
(22) PCT Filed: Dec. 13, 2010
(86) PCT No.: PCT/EP2010/069469
§ 371 (c)(1), (2), (4) Date: Jun. 15, 2012

(87) PCT Pub. No.: WO2011/073120
PCT Pub. Date: Jun. 23, 2011

(65) Prior Publication Data
US 2012/0263633 A1 Oct. 18, 2012

Related U.S. Application Data

(60) Provisional application No. 61/287,209, filed on Dec. 17, 2009.

(51) Int. Cl.
*B01D 53/94* (2006.01)
*B01J 23/40* (2006.01)
*B01J 23/42* (2006.01)
*B01J 35/00* (2006.01)
*B01J 37/00* (2006.01)

(52) U.S. Cl.
USPC ........ 423/213.5; 502/325; 502/332; 502/333; 502/339; 502/439; 502/514; 977/773; 977/810; 977/896; 977/903

(58) Field of Classification Search
USPC ............... 423/213.5; 502/325, 332, 333, 339, 502/439, 514; 977/773, 810, 896, 903
See application file for complete search history.

(56) References Cited

U.S. PATENT DOCUMENTS

| | | | |
|---|---|---|---|
| 5,491,120 A | 2/1996 | Voss et al. | |
| 5,627,124 A | 5/1997 | Farrauto et al. | |

(Continued)

FOREIGN PATENT DOCUMENTS

| | | |
|---|---|---|
| DE | 10297544 | 11/2004 |
| EP | 2177267 | 4/2010 |

(Continued)

OTHER PUBLICATIONS

"International Search Report in PCT/EP2010/069469", mailed on Mar. 28, 2011, 3 pages.

(Continued)

*Primary Examiner* — Timothy Vanoy
(74) *Attorney, Agent, or Firm* — Servilla Whitney LLC

(57) ABSTRACT

Described is a metal oxide support material containing nanoscaled iron-platinum group metal particles having a particle size in the range of 0.5 to 10 nm. At least 70% of the nanoscaled iron-platinum group metal particles are located on an outside surface layer of the metal oxide support material. The outside surface layer has an average volume of less than 50% based on the total volume of the metal oxide support material. Additionally, described is a process for preparation of metal oxide support materials containing nanoscaled iron-platinum group metal particles. Furthermore, described is the use of metal oxides containing nanoscaled iron-platinum group metal particles as catalysts, for example as a diesel oxidation catalyst for the treatment of exhaust gas emissions from a diesel engine.

18 Claims, 6 Drawing Sheets

(56) References Cited

U.S. PATENT DOCUMENTS

| | | | |
|---|---|---|---|
| 7,381,682 B1 * | 6/2008 | Jia et al. | 502/327 |
| 7,396,795 B2 * | 7/2008 | Reyes et al. | 502/150 |
| 7,521,392 B1 * | 4/2009 | Kilic et al. | 502/327 |
| 7,534,741 B2 * | 5/2009 | Wu et al. | 502/300 |
| 7,838,461 B2 * | 11/2010 | Komatsu et al. | 502/325 |
| 2005/0069648 A1 | 3/2005 | Maruyama | |
| 2007/0240792 A1 | 10/2007 | Witteler et al. | |
| 2008/0045405 A1 | 2/2008 | Beutel et al. | |
| 2008/0096986 A1 * | 4/2008 | Thomazeau et al. | 518/716 |
| 2008/0128656 A1 * | 6/2008 | Thollon et al. | 252/373 |
| 2008/0269446 A1 | 10/2008 | Michl et al. | |
| 2009/0324839 A1 | 12/2009 | Klippel et al. | |
| 2010/0180581 A1 | 7/2010 | Grubert et al. | |
| 2010/0180582 A1 | 7/2010 | Mueller-Stach et al. | |
| 2010/0285952 A1 | 11/2010 | Hofinger et al. | |
| 2011/0020170 A1 | 1/2011 | Luinstra et al. | |
| 2011/0206753 A1 | 8/2011 | Karpov et al. | |
| 2011/0245391 A1 | 10/2011 | Karpov et al. | |
| 2011/0245392 A1 | 10/2011 | Karpov et al. | |
| 2011/0251055 A1 * | 10/2011 | Fu et al. | 502/339 |

FOREIGN PATENT DOCUMENTS

| | | |
|---|---|---|
| WO | WO-2006/021308 | 3/2006 |
| WO | WO-2006/134116 | 12/2006 |
| WO | WO-2008/012248 | 1/2008 |
| WO | WO-2009/016248 | 2/2009 |
| WO | WO-2009/022544 | 2/2009 |
| WO | WO-2009/115506 | 9/2009 |

OTHER PUBLICATIONS

Ingelsten, Hanna H. et al., "Deposition of Platinum Nanoparticles, Synthesized in Water-in-Oil Microemulsions, on Alumina Supports", *Langmuir*, vol. 18 2002 , 1811-1818.

* cited by examiner

20nm 20 nm

METAL OXIDE SUPPORT MATERIAL CONTAINING NANOSCALED IRON PLATINUM GROUP METAL

CROSS-REFERENCE TO RELATED APPLICATIONS

This application is the National Stage entry of PCT/EP2010/069469, filed on Dec. 13, 2010, which claims priority to U.S. Provisional Application Ser. No. 61/287,209, filed on Dec. 17, 2009, both of which are incorporated herein by reference in their entireties.

TECHNICAL FIELD

The present invention relates to a metal oxide support material comprising nanoscaled iron-platinum group metal particles having a particle size in the range of 0.5 to 10 nm, wherein at least 70% of all nanoscaled iron-platinum group metal particles are located on a outside surface layer of the metal oxide support material, and wherein the outside surface layer has an average volume of 50% based on the total volume of the metal oxide support material.

In addition, the present invention relates to a process for preparation of such metal oxide support material containing nanoscaled iron-platinum group metal particles. Furthermore, the present invention relates to the use of metal oxides containing nanoscaled iron-platinum group metal particles as catalysts, for example as a diesel oxidation catalyst for the treatment of exhaust gas emissions from a diesel engine.

BACKGROUND

Operation of lean burn engines, e.g., diesel engines and lean burn gasoline engines, provide the user with excellent fuel economy and have very low emissions of gas phase hydrocarbons and carbon monoxide due to their operation at high air/fuel ratios under fuel lean conditions. Diesel engines, in particular, also offer significant advantages over gasoline engines in terms of their fuel economy, durability, and their ability to generate high torque at low speed.

From the standpoint of emissions, however, diesel engines present problems more severe than their spark-ignition counterparts. Emission problems relate to particulate matter, nitrogen oxides (NOx), unburned hydrocarbons (HC) and carbon monoxide (CO). NOx is a term used to describe various chemical species of nitrogen oxides, including nitrogen monoxide (NO) and nitrogen dioxide ($NO_2$), among others.

Oxidation catalysts comprising precious metals such as iron-platinum group metals (PGM) dispersed on a refractory metal oxide support are known for use in treating the exhaust of diesel engines in order to convert both hydrocarbon and carbon monoxide gaseous pollutants by catalyzing the oxidation of these pollutants to carbon dioxide and water. Such catalysts have been generally contained in units called diesel oxidation catalysts (DOC), or more simply catalytic converters, which are placed in the exhaust flow path from a diesel powered engine to treat the exhaust before it vents to the atmosphere. Typically, the diesel oxidation catalysts are formed on ceramic or metallic substrate carriers upon which one or more catalyst coating compositions are deposited. In addition to the conversions of gaseous HC, CO and the soluble organic (SOF) fraction of particulate matter, oxidation catalysts that contain iron-platinum group metals (which are typically dispersed on a refractory metal oxide support) promote the oxidation of nitric oxide (NO) to $NO_2$.

For example U.S. Pat. No. 5,491,120 discloses oxidation catalysts containing ceria and a bulk second metal oxide which may be one or more of titania, zirconia, ceria-zirconia, silica, alumina-silica and alpha-alumina.

U.S. Pat. No. 5,627,124 discloses oxidation catalysts containing ceria and alumina. It is disclosed that each have a surface area of at least about 10 $m^2/g$. The weight ratio of ceria to alumina is disclosed to be 1.5:1 to 1:1.5. It is further disclosed to optionally include platinum. The alumina is disclosed to preferably be activated alumina. U.S. Pat. No. 5,491,120 discloses oxidation catalysts containing ceria and a bulk second metal oxide, which may be one or more of titania, zirconia, ceria-zirconia, silica, alumina-silica and alpha-alumina.

The prior art shows an awareness of the use of zeolites, including metal-doped zeolites, to treat diesel exhaust. US 2008/045405 discloses a diesel oxidation catalyst for the treatment of exhaust gas emissions, such as the oxidation of unburned hydrocarbons, and carbon monoxide and the reduction of nitrogen oxides. More particularly, US 2008/045405 is directed to a washcoat composition comprising two distinct washcoat layers containing two distinctly different weight ratios of Pt:Pd.

PGMs are the catalytic active species in DOC- and Three-Way Conversion—(TWC) Applications. Usually platinum and palladium are used as active metals in diesel oxidation catalysts and a combination of platinum, palladium and rhodium as active metals in TWC-catalysts. The oxidation of CO to $CO_2$ and the oxidation of hydrocarbons to $CO_2$ is mainly catalyzed by platinum. The addition of palladium decreases the mobility of the platinum on the surface of the refractory metal oxide support, for example $\gamma$-$Al_2O_3$. In addition, in the presence of palladium the sintering of the metals particles at higher temperatures can be reduced. In the TWC application rhodium is used in addition for catalyzing the reduction of nitrogen oxide (2 NO+2 CO→$N_2$+2 $CO_2$).

The accessibility of the surface of the catalytic active species is essential for the catalytic activity. The process for the preparation of diesel oxidation catalysts known in the art comprises (i) combining platinum and palladium salts in water (ii) adding $\gamma$-$Al_2O_3$ and further additives to the solution of (i) obtaining a water-based slurry (so called washcoat). The PGM-containing washcoat is adjusted to a special viscosity. Honeycomb cordierites are coated via dip coating with a PGM-containing washcoat and calcined. The reduction of the PGM-ions takes place while driveway. The described process leads to very small metallic PGM-nanoparticles having an average diameter of 1 to 2 nm. As the noble metal solution migrates deep into the pores of the alumina, even into the innermost layer of the alumina, the later on reduced PGM nanoparticles are also deposited there. Thus, the obtained PGM containing alumina shows a uniform distribution of the PGMs. However, the PGM being in the innermost layer of the alumina are not accessible for the catalyses.

SUMMARY

Embodiments of the present invention are directed toward a metal oxide support material comprising nanoscaled iron-platinum group metal particles having a particle size from 0.5 to 10 nm, wherein at least 70% of all nanoscaled iron-platinum group metal particles are located on an outside surface layer of the metal oxide support material, and wherein the outside surface layer has an average volume of less than 50% based on the total volume of the metal oxide support material.

In one or more embodiments, the metal oxide support material is alumina, optionally doped with ceria and/or zirconia.

In one or more embodiments, the iron-platinum group metal particles are a combination of platinum and palladium or a combination of platinum, palladium and rhodium.

In one or more embodiments, the particle size of the iron-platinum group metal particles is from 0.5 to 4 nm.

In one or more embodiments, at least 80% of the nanoscaled iron-platinum group metal particles are located on the outside surface layer of the metal oxide support material, and the outside surface layer has an average volume of 20% based on the total volume of the metal oxide support material.

A second aspect of the present invention is directed to a process for the preparation of a metal oxide support material comprising a nanoscaled iron-platinum group metal, the process comprising (i) dissolving a precursor of the iron-platinum group metal and a polymer in water and/or an organic solvent, (ii) reducing the precursor of the iron-platinum group metal, optionally adding a reducing reagent, and (iii) combining the solution obtained in (ii) with a metal oxide support material.

A further aspect of the present invention is directed to a process for the preparation of a metal oxide support material comprising a nanoscaled iron-platinum group metal, the process comprising (i) dissolving a precursor of the iron-platinum group metal and a polymer in water and/or an organic solvent containing a metal oxide support material, and (ii) reducing the solution of (i).

In one or more embodiments, the precursor of the iron-platninum group metal is an iron-platinum metal salt selected from the group consisting of nitrates, hydroxides, oxides or as amine complexes or as acetylacetonates or acetates.

In one or more embodiments, the polymer is selected from derivatized polyethyleneimines or polyvinylamines, linear or cross linked homo- and/or copolymers of vinyl lactams, vinylimidazoles, vinylacetate or vinyl formaamide, linear or cross linked graft-homo and/or graft-copolymers, vinyl lactams, vinylimidazoles, vinylacetate or vinyl formamide on polyether, linear or cross linked water soluble or water dispersable polymers with acidic groups, such as carboxylate, phosphonic or sulfonic groups.

A still further aspect of the present invention is directed to a method of hydrogenating, dehydrogenating, oxidizing, metathesizing, and/or dealkylating, the method comprising using a metal oxide support material comprising a nanoscaled metal particle according to the invention as a catalyst.

A yet further aspect of the present invention is directed to a diesel oxidation catalyst for the treatment of exhaust gas emissions from a diesel engine, wherein the metal oxide support material comprising nanoscaled metal particles according to the invention are disposed on a carrier substrate.

A yet further aspect of the present invention is directed to a method for treating diesel engine exhaust gas stream emissions, the method comprising contracting the exhaust stream with the diesel oxidation gas catalyst of the invention.

DETAILED DESCRIPTION

Figure 1:
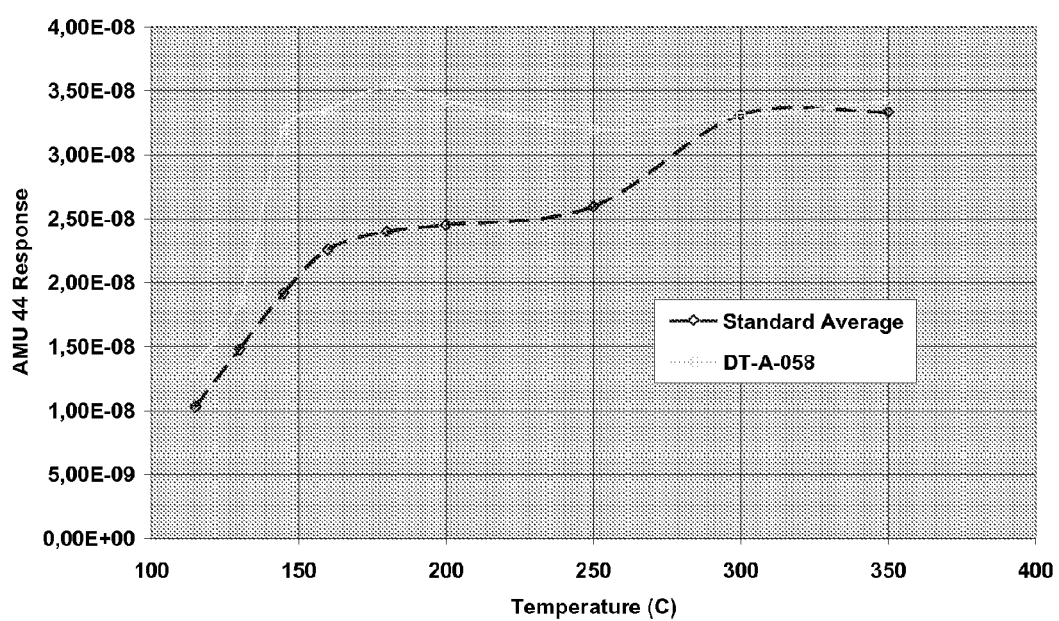
FIG. 1: Powder test of TM 100/150 decorated with 2.2 wt.-% Pt: detection of $CO_2$ (given in AMU response) vs. temperature (sample No DT_A_058).

It is also a goal to control the location of the active metals on the metal oxide support material in such a way that the accessibility/availability is optimized resulting in improved performance of the diesel oxidation catalyst.

Therefore, the present invention relates to a metal oxide support material comprising nanoscaled iron-platinum group metal particles having a particle size in the range of 0.5 to 10 nm, wherein at least 70% of the nanoscaled iron-platinum group metal particles are located on an outside surface layer of the metal oxide support material, and wherein the outside surface layer has an average volume of 50% based on the total volume of the metal oxide support material.

As used in this specification and the appended claims, the singular forms "a", "an" and "the" include plural referents unless the context clearly indicates otherwise. Thus, for example, reference to "an iron-platinum group metal" includes a mixture of two or more metals from the iron-platinum group, and the like.

As used in this specification and the appended claims, the term "iron-platinum group" includes all metals from the iron-, the cobalt- and the platinum groups. Therefore the iron-platinum group contains iron, cobalt, nickel, ruthenium, rhodium, palladium, osmium, iridium, platinum, hassium, meitnerium, darmstadtium.

Metal Oxide:

Suitable metal oxide support materials are known to the person skilled in the art. In one or more embodiments, the metal oxide support material is a base metal oxide and/or transition metal oxide selected from the group including compounds of silica, alumina, zirconia, titania and mixtures thereof. In one or more embodiments, the supports are activated, high-surface area compounds selected from the group consisting of alumina, zirconia, silica, titania, silica-alumina, zirconia-alumina, titania-alumina, lanthana-alumina, lanthana-zirconia-alumina, baria-alumina, baria-lanthana-alumina, baria-lanthana-neodymia-alumina, zirconia-silica, titania-silica, zirconia-titania.

For diesel oxidation catalysts, alumina supports, optionally doped with rare earth metals, are preferred. Commercial available alumina support materials are SBA-150 ($\gamma Al_2O_3$ with a primary particle size of 5-75 nm, BET: 137 m$^2$/g), TM (100/150) ($\gamma Al_2O_3$ with a primary particle size of 5-90 nm, BET: $^-$150 m$^2$/g), SBA-70 ($\delta$-$Al_2O_3$ with a primary particle size of 5-70 nm (very rarely 370 nm), BET: 85.5 m$^2$/g), Siralox1,5/100 ($\delta$-$Al_2O_3$ with a primary particle size of 5-50 nm, BET: 102 m$^2$/g) or KR 70 ($\gamma$-$Al_2O_3$ with a primary particle size of 5-90 nm, BET: 155 m$^2$/g).

Doping:

The metal oxide may be doped with other metals, preferably doped with ceria and/or zirconia. In one or more embodiments, the doping conditions are dependent on the application and known to a person skilled in the art.

Porosity:

In one or more embodiments, the metal oxide support material exhibit a BET surface area, determined according to DIN 66131, from about 30 to about 160 m²/g. The porosity is adjusted to the special application.

Pore Size:

In one or more embodiments, the metal oxide material exhibits a pore size from about 0.3 to about 5 nm, preferable from about 0.5 to about 4 nm, even more preferred from about 0.5 to about 2 nm. Preferably the metal oxide material exhibits an average pore diameter from about 70 Å to about 150 Å.

Particle Size:

In one or more embodiments, the metal oxide support material has a particle size from about 5 to about 200 nm, even more preferred from about 5 to about 100 nm. Even more preferred the particle size is in the range from about 30 nm to about 90 nm Agglomerates:

Optionally the metal oxide support material is present as an agglomerate, whereas preferably the agglomerates have an average diameter of about 100 nm to about 20 mlcrometer, even more preferred of about 500 nm to about 15 micrometer.

If the metal oxides are present as agglomerates, the specifications to the location of the nanoscaled particles relate to the agglomerates as such. Thus, if the metal oxides are present as agglomerates, at least 70% of all nanoscaled iron-platinum group metal particles are located on a outside surface layer of the metal oxide support material agglomerates, whereas the outside surface layer of the agglomerates has an average volume of less than 50% based on the total volume of the agglomerates.

Nanoscaled Iron-Platinum Group Metal Particles:

Suitable iron-platinum group metal particles are known to the person skilled in the art. Optionally, the iron-platinum group metal or the combination of iron-platinum group metals may be doped with other co-metals.

For DOC application, in one or more embodiments, platinum is used as active metal for the oxidation catalyses. In a specific embodiment, a combination of platinum and palladium is used. In one or more embodiments, the weight ratio of platinum to palladium is from about 10:1 to about 0.5:1, more preferred from about 5:1 to about 0.5:1, even more preferred from about 2:1 to about 1:1. In case of combinations, the metal particles may be present as alloy, core-shell or bi or tri-phasic particles or mixtures of these.

For TWC application, in one or more embodiments, a combination of platinum, palladium and rhodium is used as active metals. In one or more embodiments, weight ratios of platinum to palladium to rhodium are known to the skilled person in the art. In case of combinations, the metal particles may be present as alloy, core-shell or bi or tri-phasic particles or mixtures of these.

For hydrogenation applications, in one or more embodiments, a combination of rhodium and nickel is used as active metals.

For fuel cell applications, in one or more embodiments, platinum is used as active metal.

For $NO_x$ reduction applications, in one or more embodiments, palladium is used as active metal.

For steam dealkylation applications, in one or more embodiments, iridium is used as active metal.

In addition to active metals belonging to the iron-platinum group metal, for formaldehyde-synthesis, silver may be used analogously to the present invention.

Particle Size:

In one or more embodiments, the particle size ($d_{50}$) of the nanoscaled iron-platinum group metal particle is from about 0.5 to about 5 nm. Preferred the particle size is from about 0.5 to 2 nm.

Amount:

In one or more embodiments, metal oxide support material contains the nanoscaled iron-platinum group metal particles in an amount from about 0.1 to about 10 wt.-%, more preferred from about 1 to about 5 wt.-%, based on the weight of the metal oxide support material.

Percentage:

In one or more embodiments, at least 80% of all nanoscaled iron-platinum group metal particles are located on the outside surface layer of the metal oxide support material or agglomerates thereof, wherein the outside surface layer has an average volume of 50% based on the total volume of a primary support material particle. In a specific embodiment, at least 90% of all nanoscaled iron-platinum group metal particles are located on the outside surface layer. In a more specific embodiment, at least 95% of the nanoscaled iron-platinum group metal particles are located on the outside surface layer.

In one or more embodiments, 80 to 100% of all nanoscaled iron-platinum group metal particles are located on the outside surface layer. In a specific embodiment, 90 to 100% of all nanoscaled iron-platinum group metal particles, in a more specific embodiment, 95 to 100% of the nanoscaled iron-platinum group metal particles are located on the outside surface layer, wherein the outside surface layer has an average volume of 50% based on the total volume of the metal oxide support material or agglomerates thereof.

Dimension of Outside Surface Layer:

In one or more embodiments, the outside surface layer has an average volume of 40% based on the volume of the metal oxide support material or agglomerates thereof. In a specific embodiment, the outside surface layer has an average volume of 30%, more specifically a volume of 20%, even more specifically a volume of 10%, based on the total volume of the metal oxide support material or agglomerates thereof.

The concentration/loading of nanoscaled iron-platinum group metal particles on the outside surface layer of the metal oxide can be determined by gradually shaving off the metal oxide support material containing nanoscaled iron-platinum group metal particles of this invention from the outside surface to the inner layers thereof, and measuring the content (weight) of the nanoscaled iron-platinum group metal particles per unit weight of the metal oxide support material containing nanoscaled iron-platinum group metal particles so shaven.

Combination of Percentage and Dimension of Outside Surface Layer:

In one or more embodiments, at least 80% of the nanoscaled iron-platinum group metal particles are located on the outside surface layer of the metal oxide support material or agglomerates thereof, wherein the outside surface layer has an average volume of 30%, based on the total volume of the metal oxide support material or agglomerates thereof. In a specific embodiment, at least 90% of the nanoscaled iron-platinum group metal particles are located on the outside surface layer of the metal oxide support material, wherein the outside surface layer has an average volume of 20%, based on the total volume of the metal oxide support material or agglomerates thereof.

Process for Preparation Such Metal Oxides Containing Nanoscaled Metal Particles

This invention also relates to a process for preparation of metal oxide support material containing nanoscaled iron-platinum group metal, the process comprising:

(i) dissolving a precursor of iron-platinum group metal(s) and a polymer in water and/or an organic solvent, (ii) reducing the precursor of the iron-platinum group metal(s) optionally adding a reducing reagent, and (iii) combining the solution obtained in (ii) with a metal oxide support material
or
(i) dissolving a precursor of the iron-platinum group metal and a polymer in water and/or an organic solvent containing metal oxide support material,
(ii) reducing the solution of (i).

Precursor of the Iron-Platinum Group Metal:

Generally, all suitable sources for precursor of the iron-platinum group metal known to a person skilled in the art can be employed. By way of example, the precursor is a corresponding iron-platinum group metal salt, such as salts of acetylacetonate, nitrates, acetates or bound also amine complexes in nitrate or hydroxyl salts. Also the conesponding acids can be used. These metals may be present in the form of their oxides, nitrates, phosphates, sulfates, sulfites, phosphonites, nitrites, borates, aluminates, silicates, cyanides, isocyanates, thioisocyanates, perchlorates, periodates, perbromates, chlorates, iodates, bromates, hypochlorites or in the form of complex compounds. In one or more embodiments, the nitrates and the amino-complexes of platinum, palladium and/or rhodium are used.

Polymer:

Suitable polymers have one or more functional groups. In one or more embodiments, functional groups are corboxylates, carboxylic acids, gluconic acids, amines, imines, amides, pyrrolidones, imidazoles, caprolactams, esters, urethanes, ureas derivatives, and/or amine ethers. These polymers bind to the metal surface and control the size of the metal particles. In addition, the polymers possess a binding ability to the metaloxide support material which hinders the metal particles for migration into the insight of the support material and leads to an enrichment of the catalytic active species on the metal oxide support surface.

Suitable polymers are derivates of polyethyleneimines or polyvinylamines, based on homopolymers of ethyleneimine (aziridine), graft polymers of polyamidoamines with ethyleneimine, graft polymers of polyvinylamines with ethyleneimine, polymers of the higher homologs of ethyleneimine, at least partly hydrolyzed N-vinylcarboxamide homopolymers or at least partly hydrolyzed N-vinylcarboxamide copolymers as described in more detail in WO 2009/115506.

As described in WO 2009/115506, these base polymers are preferred functionalized by 1,4-Addition (Michael addition) onto alpha,beta-unsaturated carbonyl compounds. Suitable alpha,beta-unsaturated carbonyl compounds are acrylic acid and acrylates, for example alkyl acrylates and hydroxyalkyl acrylates, methacrylic acid and methacrylates, for example alkyl methacrylates and hydroxyalkyl methacrylates, acrolein, arylamides and acrylonitrile. And/Or in a reaction with epoxides, diepoxides, halohydrin ethers and/or bishalohydrin ethers; suitable diepoxides are, for example, 1,6-hexanediol bisglycidyl ether and bisglycidyl ethers of oligo- and polyethylene glycols; and reaction products of halohydrins, for example epichlorohydrin, with alkylene glycols and polyalkylene glycols having 2 to 100 ethylene oxide or propylene oxide units and/or reaction with isocyanates; for example with diisocyanates, such as hexamethylene diisocyanate, isophorone diisocyanate, dicyclohexylmethane 4,4'-diisocyanate and diphenylmethane diisocyanate.

In one or more embodiments, polyethyleneimines, the derivatives of which are used according to WO 2009/115506, are the homopolymers of ethyleneimine and the graft polymers of polyamidoamines with ethyleneimine. In a specific embodiment, polyethyleneimines and graft polymers of polyamidoamines with ethyleneimine are those having a molecular weight in the range from 500 to 2 000 000 g/mol, particularly preferably from 1000 to 100 000 g/mol, in particular from 5000 to 50 000 g/mol.

In a special embodiment these polyethyleneimines are reacted with a diepoxide and/or bischlorohydrin ether and then reacted with one or more alpha,beta-unsaturated carbonyl compounds; for example, they are reacted with 1,6-hexanediol bisglycidyl ether or bisglycidyl ether of a polyalkylene glycol and then with (meth)acrylic acid, 2-acrylamidoglycolic acid, alkyl (meth)acrylate, for example methyl acrylate, and/or hydroxyalkyl (meth)acrylate, for example hydroxyethyl acrylate or 4-hydroxybutyl acrylate.

In addition, water soluble or water dipersable homopolymers, copolymers, graft-homo and graft copolymers of vinylic monomers, vinylic comonomers and possibly bi- or multi-functional vinylic monomers are preferred as described in more detail in the European Application filed on 15 Dec. 2009 having the Application Number 09179279.6 and in the European Application filed on 22 Dec. 2008 having the Application Number 08172552.5.

These polymers may also be present as di- or multi-block copolymers, in a star, brush or hyperbranched form or as dendrimers.

In one or more embodiments, the monomers are vinyllactams like N-vinylpyrrolidone, 3-methyl-N-vinylpyrrolidone, 4-methyl-N-vinylpyrrolidone, 5-methyl-N-vinylpyrrolidone, N-vinylpiperidone and N-vinylcaprolactam, vinylacetate as well as its hydrolysis product after the polymerization vinylalkohol, vinylamide and vinylformamide as well as its hydrolysis product after the polymerization vinylamin, N-vinylimidazole, Isopropylmethacrylamide, vinylmethylamide, acrylamide, methacrylamide and 2-hydroxyethylacrylamide.

In one or more embodiments, the copolymers are N-vinyllactam like N-vinylpyrrolidone, 3-methyl-N-vinylpyrrolidone, 4-methyl-N-vinylpyrrolidone, 5-methyl-N-vinylpyrrolidone, N-vinylpiperidone and N-vinylcaprolactam, vinylamide like vinylformamide as well as its hydrolysis product after the polymerization vinylamine, N-vinylimidazole, isopropylmethacrylamide, vinylmethylamide, acrylamide, methacrylamide, 2-hydroxyethylacrylamide and 2-hydroxyethylmethacrylamide, further 1-vinyl-3-methylimidazoliume chloride, vinylester of aliphatic C2-C18-Carbonic acids like vinylacetate, as well as its hydrolysis product after the polymerization vinylalkohole, vinylpropionate, vinylbutyrate, vinyllaurate, vinylstearate, vinylneodecanoat vEOvA 9 and vEOvA 10, further dimethylaminoethyl(meth)acrylate and dimethylaminoethyl(meth)acrylamide and their quaternized analoga and plus diallyldimethylammoniumchloride.

In one or more embodiments, the bi- or multi-functional vinylic monomers are pentaerythrittriallylether, methylen-bis-acrylamide, N,N'-divinylethylenurea, divinylbenzole, ethylen-bis-N-vinylpyrrolidone, 3-vinyl-N-vinylpyrrolidone, 4-vinyl-N-vinylpyrrolidone, 5-vinyl-N-vinylpyrrolidone, allyl(meth)acrylate, triallylamine and acryl ester of glykoel, butandiole, trimethylolpropane or glycerine as well as acryl ester of ethylenoxideand/or epichlorhydrins modified glycole, butandiole, trimethylolpropane or glycerine.

In one or more embodiments, the constituent amount of the monomers is from about 20 to about 100 wt.-% based on weight percentage related to the total mass of polymers, preferred from about 30 to about 100 wt.-%, particularly preferred from about 50 to about 100 wt.-%, and in particular preferred from about 60 to about 100 wt.-%.

In one or more embodiments, the constituent amount of the co-monomers is from about 0 to about 80 wt.-%, based on weight percentage related to the total mass of polymers, preferred from about 0 to about 70 wt.-%, particularly preferred from about 0 to about 50 wt.-% and in particular preferred from about 0 to about 40 wt.-%.

In one or more embodiments, the constituent amount of the bi or multi-functional vinylic monomers is from about 0 to about 20 wt.-%, based on weight percentage related to the total mass of polymers, preferred from about 0 to about 10 wt.-%, particularly preferred from about 0 to about 5 wt.-% and in particular preferred from about 0 to about 1 wt.-%.

Also preferred are polyether-containing graft polymers of polyether and one or more vinylic monomers of vinyllactams like N-vinylpyrrolidone and N-vinylcaprolactam, vinylamines like N-vinylimidazole, N-vinylformamide and as its hydrolysis product after the polymerization vinyl amine.

In addition, mixtures of polymers described above are preferred in this invention.

Equally suitable are linear or crosslinked water soluble or water dispersable polymers with acidic groups; for example, a homo or copolymer of (meth)acrylic acid and other acidic monomers, such as maleic acid, itaconic acid and/or vinylphosphonic acid. The copolymer may furthermore optionally comprise further monomers without acidcontaining groups. As described in WO2006/134116, WO 2006/021308 and WO 2008/012248.

Water or an Organic Solvent:

The reduction can be carried out in organic solvents, such as alcohols, polyols, esters, chlorohydrocarbons, phenols, DMSO, DMF, NMP and ethers, such as THF, dioxane or dioxolane. Other reaction media are also conceivable, such as salt melts or ionic liquids. Water or aqueous organic solvent mixtures, glycol and diethylene glycol are preferred solvent, and water and aqueous organic solvent mixtures are particularly preferred.

Reducing Agent:

In stage (ii) optionally a reducing agent is added. In one or more embodiments, a reducing agent is added if the precursor of the iron-platinum group metal and the polymer are dissolved in water or an organic solvent other than alcohol or a polyol. Generally, all suitable reducing agents known to a person skilled in the art can be employed. Suitable reducing agents may be organic or inorganic reducing agents. Examples are alcohols, such as methanol or ethanol, amino alcohols, such as 1,2-aminoethanol, diethanolamine, aldehydes, such as formaldehyde or acetaldehyde, ketones, carboxylic acids, such as formic acid, acetic acid or oxalic acid, alkenoic acids, such as 5-pentenoic acid, hydrazine or hydrazine derivatives, azo compounds, such as AIBN (azobisisobutyronitrile), carboxylic anhydrides, amides, amines, ethers, esters, alkenes, dienes, thio compounds, mono- or polysaccharides, hydrogen or oxides of carbon. Suitable inorganic reducing agents are hydrogen, metals, such as zinc, calcium and magnesium, and metal hydrides, such as sodium borohydride, and Fe(II) salts, thiosulfates, thiosulfites, sulfides and disulfides.

Formic acid, formaldehyde, diethanolamine, methanol, ethanol, 5-pentenoic acid, ascorbic acid, citric acid, lactic acid, oxalic acid, glucose, fructose and sodium borohydride are preferred. In one or more embodiments, the organic reducing agents are diethanolamine, 5-pentenoic acid, ascorbic acid glucose and citric acid. In specific embodiments, formic acid or formaldehyde are particularly preferred. Carbon dioxide forms thereby and can be easily removed from the reaction mixture. For example, carbon dioxide can be removed from the reaction mixture by stripping with air.

In one or more embodiments, the inorganic reducing agents are sodium borohydride, Sn(II) salts, Fe(II) salts, thiosulfates, thiosulfites, phosphites, phosphanes, sulfides and disulfides.

Without Reducing Agent:

In one embodiment of the present invention an alcohol is used as solvent and as reducing agent. Thus, if the reaction is already performed in an alcoholic media, no additional reducing reagent has to be added.

In one or more embodiments, poylols are used as both solvent and reducing agent. In a specific embodiment, the polyols are diethylene glycol, propylene glycol, butylene glycol, ethylene glycol and/or glycerine. The poylols act as stabilizers. The multible OH-groups coordinate to the emerging PGM nanoparticle in a very early phase, which hinders an uncontrolled growing. This technique, however, leads to very small nanoparticles.

In one or more embodiments, short chained aliphatic diols are used for this process, for example 1,2-ethanediol, 1,2-propanediol, 1,3-propandiol, 1,2-butynediol, 2,3-butynediol, 1,4-butynediol, 1,2-pentanediol, 2,4-pentanediol.

Polyether-homopolymere featuring OH-groups are also Preferred:

Polyethylenglycol, polypropylenglycol and polybutylenglykol, binary copolymers like ethylenglykol/propylenglykol- and ethylenglykol/butylenglykol-copolymers, not branched ternary copolymers like ternary ethylenglycol/propylenglycol/ethylenglycol-, propylenglycol/ethylenglykol/propylenglcol- and ethylenglycol/butylenglykol/ethylenglycol-copolymers.

Suitable diols are polyether-blockcopolymers with an OH-functionality like binary blockcopolymers like polyethylenglycol/polypropylenglycol and polyethylenglykol/polybutylenglycol, not-branched alkyl chained, ternary blockcopolymers like polyethylenglycol/polypropylenglykol/polyethylenglycol, polypropylenglycol/polyethylenglycol/poly-propylenglycol and polyethylenglycol/polybutylenglycol/polyethylenglycol-terpolymers.

The mentioned polyether might be substituted and/or feature an OH-end group [literature: DE 102 97 544—chapter [0039] to [0046]].

Reaction Conditions:

The metal nanoparticles are generally prepared by reduction at temperatures of from −30 to 300° C. and pressures of from 10 mbar to 100 bar, preferably at temperatures of from 0 to 100° C., particularly preferably from 20 to 95° C., even more preferred from 50 to 85° C. Atmospheric pressure is preferably employed, so that special vacuum apparatuses or pressurized containers are not required.

Coating and Posttreatment:

The coating of metal oxide support material is well known to a person skilled in the art. Commonly, the PGM containing metal oxide support material is coated on a substrate, for example a cordierite honeycomb (monolith) using a washcoat slurry. The impregnated monolith is calcined, calcination conditions are well known in the art. During calcination, the polymer is burning off.

Depending on the application, for example DOC or TWC, additional layers (like zeolithes etc.) might be added to the substrate (see for example U.S. 61/145,367 and U.S. 61/145,413).

Use of Such Metal Oxides Containing Nanoscaled Metal Particles:

In addition, the present invention relates to the use of metal oxides comprising nanoscaled iron-platinum group metal particles as catalysts. In one or more embodiments, the metal oxides containing nanoscaled iron-platinum group metal particles catalyze hydrogenation, dehydrogenations reactions, oxidations, and metathesis or dealkylation reactions. In specific embodiments, the metal oxides comprising nanoscaled iron-platinum group metal particles are used as catalysts in the exhaust gas stream purification of cars and trucks, wherein the stream typically contains hydrocarbons, carbon monoxide, and oxides of nitrogen.

Diesel Oxidation Catalyst:

In addition, the present invention is also directed to a diesel oxidation catalyst for the treatment of exhaust gas emissions from a diesel engine, wherein the metal oxides containing nanoscaled iron-platinum group metal particles are disposed on a carrier substrate.

The substrate may be any of those materials typically used for preparing catalysts, and will preferably comprise a ceramic or metal honeycomb structure. Any suitable substrate may be employed, such as a monolithic substrate of the type having fine, parallel gas flow passages extending there through from an inlet or an outlet face of the substrate, such that passages are open to fluid flow there through (referred to herein as flow-through substrates). The passages, which are essentially straight paths from their fluid inlet to their fluid outlet, are defined by walls on which the catalytic material is coated as a washcoat so that the gases flowing through the passages contact the catalytic material. The flow passages of the monolithic substrate are thin-walled channels, which can be of any suitable cross-sectional shape and size such as trapezoidal, rectangular, square, sinusoidal, hexagonal, oval, circular, etc.

A suitable ceramic substrate may be made of any suitable refractory material, e.g., cordierite, cordierite-alumina, silicon nitride, silicon carbide, zircon mullite, spodumene, alumina-silica magnesia, zircon silicate, sillimanite, magnesium silicates, zircon, petalite, alumina, aluminosilicates and the like. The carrier substrates useful for the catalysts of the present invention may also be metallic in nature and be composed of one or more metals or metal alloys.

Method of Treating Diesel Engine Exhaust Gas Stream Emissions:

The present invention is also directed to a method for treating diesel engine exhaust gas stream emissions containing unburned hydrocarbons (HC) and carbon monoxides (CO). An exhaust gas stream from a diesel engine can be treated in an emission treatment device containing the diesel oxidation catalyst of the present invention.

The diesel oxidation catalyst (DOC) of the present invention can be used in an integrated emission treatment system comprising one or more additional components for the treatment of diesel exhaust gas emissions. For example, the emission treatment system may further comprise a soot filter component (used for removal of particulate matter) and/or a selective catalytic reduction (SCR) component (use for reduction of NOx components). The diesel oxidation catalyst can be located upstream or downstream from the soot filter and/or selective catalytic reduction component.

FIG. 1: Powder test of TM 100/150 decorated with 2.2 wt.-% Pt: detection of $CO_2$ (given in AMU response) vs. temperature (sample No DT_A__058)

Figure 2:
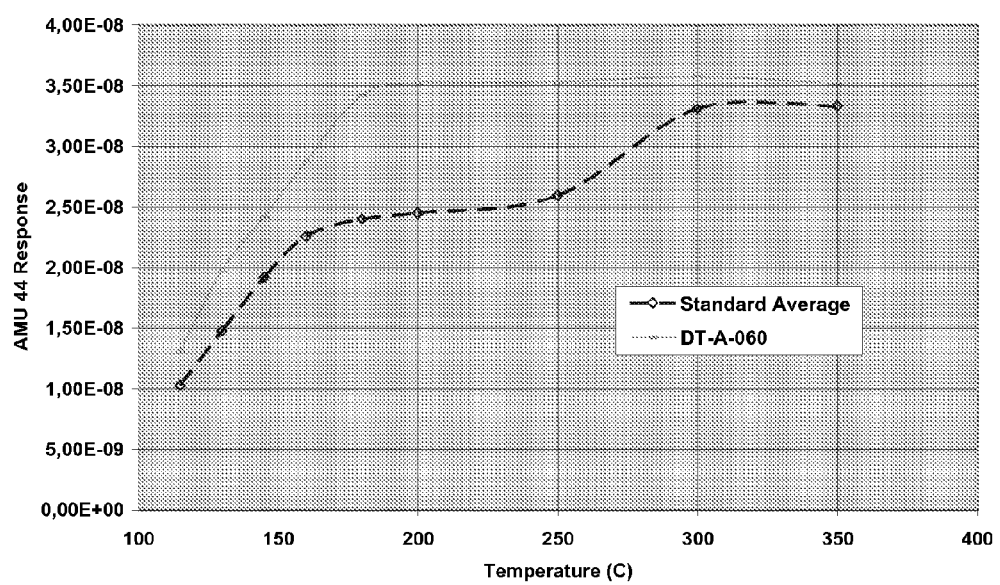
FIG. 2: Powder test of TM 100/150 decorated with 1.4 wt.-% Pd and 0.16 wt.-% Pt): detection of $CO_2$ (given in AMU response) vs. temperature.
Figure 3:
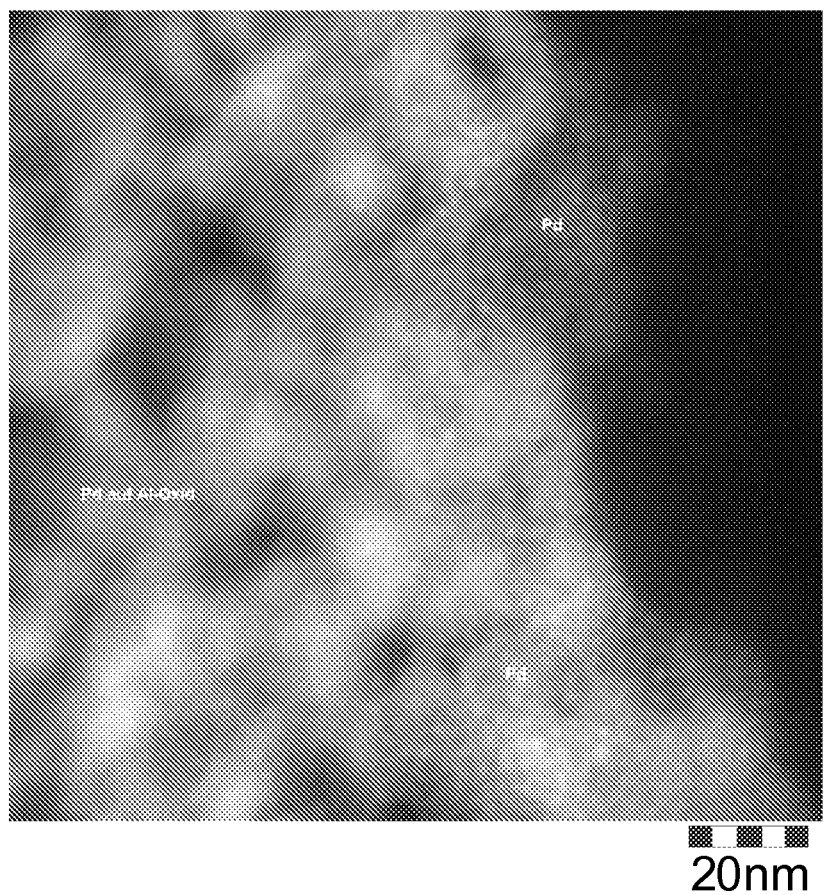
FIG. 3: TEM (HAADF-STEM), resolution 100E6:1 of the sample DT_A_058: the light areas are the PGM particles.

FIG. 2: Powder test of TM 100/150 decorated with 1.4 wt.-% Pd and 0.16 wt.-% Pt): detection of $CO_2$ (given in AMU response) vs. temperature FIG. 3: TEM (HAADF-STEM), resolution 100E6: 1 of the sample DT_A__058: the light areas are the PGM particles.

Figure 4:
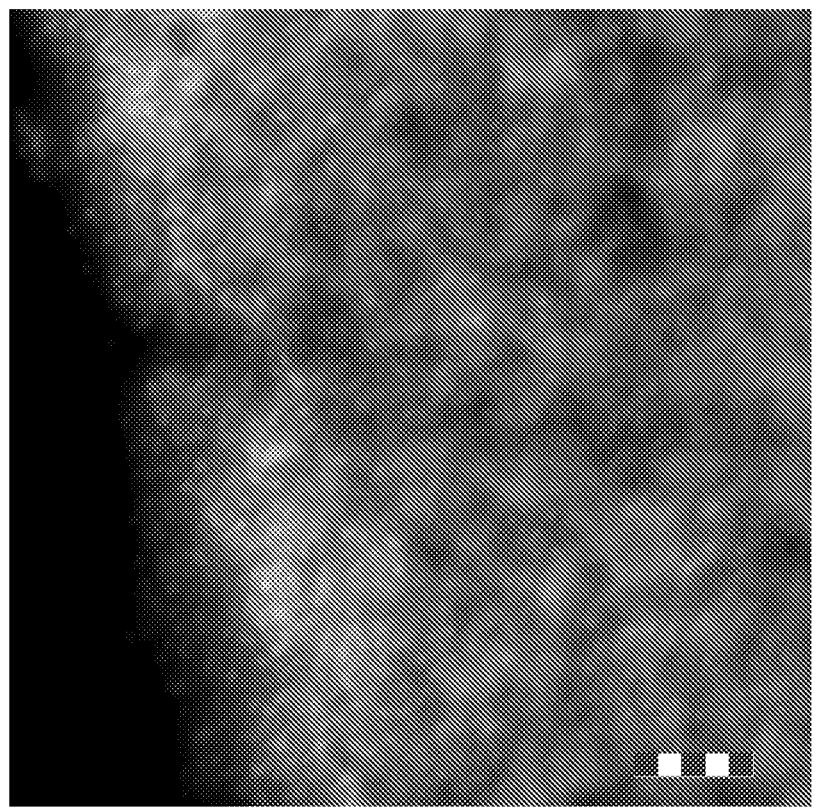
FIG. 4: TEM (HAADF-STEM), resolution 100E6:1 of the sample DT_A_060: the light areas are the PGM particles.

FIG. 4: TEM (HAADF-STEM), resolution 100E6: 1 of the sample DT_A__060: the light areas are the PGM particles.

Figure 5:
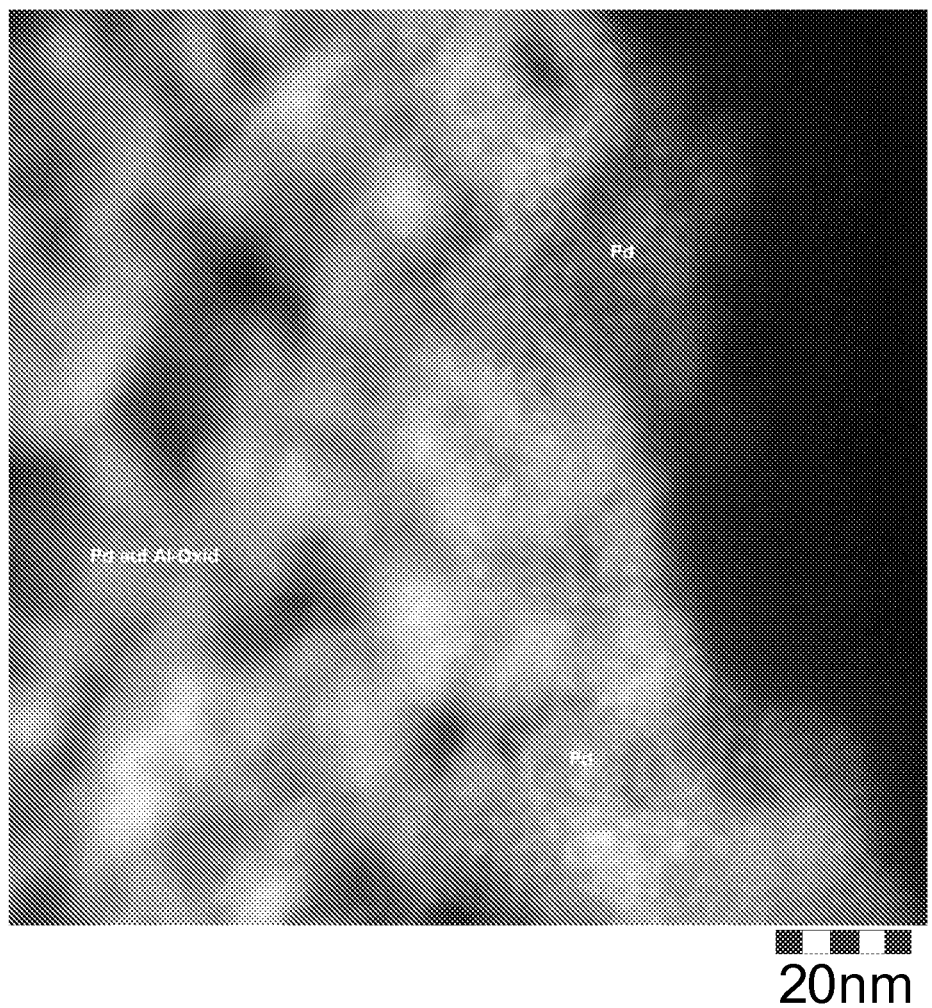
FIG. 5: TEM (HAADF-STEM), resolution 100E6:1 of the sample LJ20080124/3 on Alumina SBA 150: the light dots are the PGM particles.

FIG. 5: TEM (HAADF-STEM), resolution 100E6: 1 of the sample LJ20080124/3 on Alumina SBA 150: the light dots are the PGM particles FIG. 6: Powder test of SBA 150 decorated with 2 wt.-% Pd: detection of CO2 evolution (given in AMU response) vs. temperature

EXAMPLES

1. Preparation of Pt-Catalysts (2.2 wt.-% Pt-loading on TM 100/150) for the reaction $CO \rightarrow CO_2$ (LJ No. DT_A__058)

0.21 g Pt-acetylacetonate (98% ACROS Lot-No. A025558) and 0.0506 polyvinylpyrrolidone K 30 (Sigma Aldrich Lot-No. 85, 655-8) were dissolved in 10 g diethylene glycol (99% von Sigma-Aldrich Lot-Nr.: S46287-078). Parallel, 4.3 g Puralox (SASOL, TM 100/150, Lot B25735) were dispersed in 45 g diethylene glycol with an ultra turrax and heated up to 80° C. Then, the Pt-containing solution is added quickly. The whole suspension is stirred intensely for 2 h. After that, the diethylene glycol is removed in the vacuum (10 mbar, 100° C.) and the resulting powder is calcined at 1 h at 540° C. (rate of heating: 0.5° C./min till 350° C.; 2° C./min till 540° C.; nitrogen atmosphere).

The catalytic testing was performed using a high throughput reactor as described in item 4. The performance is compared to a standard catalyst as described in 5. The catalytic performance is shown in FIG. 1.

2. Preparation of a Pd/Pt-Catalyst (1.4 wt.-% loading of Pd and 0.16 wght.-% loading of Pt) for the reaction $CO \rightarrow CO_2$ (LJ No. DT_A__060)

0.0341 g Pt-acetylacetonate (98% ACROS, Lot-No. A0255558) and 0.2003 g Pdacetate (47% Pd, Fluka, Lot-No. 1338573) were dissolved with 0.0563 g polyvinylpyrrolidone K 30 (Sigma Aldrich, Lot-No. 85, 655-8) in 5 g diethylene glycol. Parallel a suspension of 5 g Puralox (SASOL, TM 100/150, Lot B25735) were mixed with an ultra turrax with 50 g diethylene glycol. This suspension is heated up to 80° C. and at this temperature, the precious metal solution is added. The whole slurry is heated for 2 h at 80° C. After that, the diethylene glycol is removed in the vacuum (10 mbar, 100° C.) and the resulting powder is calcined at 1 h at 540° C. (rate of heating: 0.5° C./min till 350° C.; 2° C./min till 540° C.; nitrogen atmosphere).

The catalytic testing was performed using a high throughput reactor as described in item 4. The performance is compared to a standard catalyst as described in 5. The catalytic performance is shown in FIG. 2.

3. Preparation of Pt-catalysts (LJ20080124/3)

3.1 Preparation of the Polymer A:

150 g of a 24.9% strength aqueous solution of polyethylene imine ($M_w$=25 000, cross linked with 4.55% of bisglycidyl ether of a polyethylene glycol having an average molar mass of 2000) and 202.3 g of demineralized water are initially taken in a fournecked flask having an intensive stirrer and reflux condenser and are heated to an internal temperature of 95° C. with stirring. Air is passed in continuously in the process. When the temperature of 95° C. has been reached, 66.5 g of acrylic acid are added drop wise in the course of 2 hours. Thereafter, the experiment is stirred for a further 6 hours at 95° C. The product is a light yellow, viscous solution. The K value is 21.97; yield: 100%; SC: 39.8% (after 2 hours at 120° C. under reduced pressure).

3.2 Preparation of Pt-Catalysts 17 g of Polymer A (concentration 100 g/l), 101.6 g of a 4.366% strength solution of tetra amine palladium (II) nitrate and 5.5 ml water were mixed in 500 ml 4 neck flask, equipped with an over head stirrer and a reflux condenser and thermometer, were stirred and heated to 77° C. Than, 25.3 g of a solution of ascorbic acid (concentration 300 g/l) were added and the reaction was held at 77° C. for 24 h resulting in a dark brownish black dispersion.

The TEM analysis revealed that the preparation resulted in crystalline particles with 40 nm and ca. 3 nm sizes.

3.3 Coating of alumina SBA 150 (Loading: 2 wt-% of Pd on $Al_2O_3$)

The alumina was filled in an open beaker and was thoroughly stirred while the palladium nanoparticle dispersion was added subsequently over time. Resulting in a brownish suspension, which was dried at 90° C. for 16 h and homogenized on a plate vibrator for another 30 minutes. The coated alumina was than calcined and aged at 650° C. (25 h, 10% steam) and analyzed.

The TEM resulted in metal oxide particles which posses a palladium nanoparticle enriched surface in shown in FIG. 5.

3.4 Sample Preparation for Catalytic Measurements

Then the resulting powders were pressed into pellets and their catalytic activity was evaluated (conditions: 1500 ppm CO, 500 ppm propene, 5% water, 10% oxygen). Which revealed an improved catalytic performance with respect to the standard (preparation: incipient wetness; 4 wt-% of Pd and Pt mixture 1:2).

Figure 6:
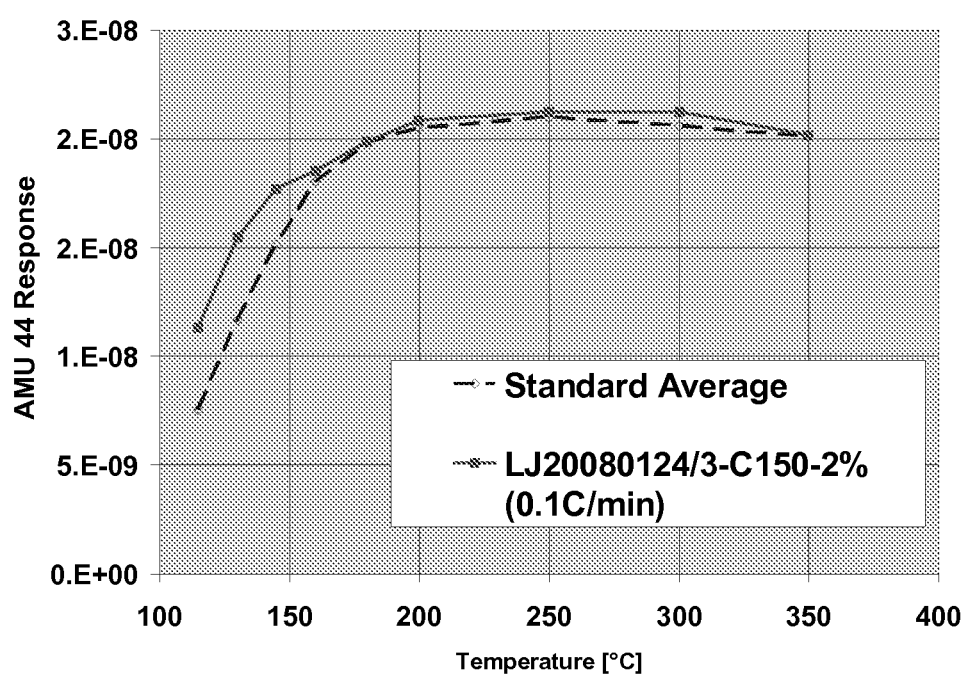
FIG. 6: Powder test of SBA 150 decorated with 2 wt.-% Pd: detection of CO2 evolution (given in AMU response) vs. temperature.

The catalytic testing is performed using a high throughput reactor as described in item 4. The performance is compared to a standard catalyst as described in 5. The catalytic performance is shown in FIG. 6.

4. High Throughput Reactor

The high throughput reactor is set to a flow rate of 1.500 ppm CO, 500 ppm propene, 5% water, 10% $O_2$ into each ceramic pellet tray.

The gases flow into the inlet, pass trough the baffles for mixing and fitribution and then flow over each sample. The exit gases are analyzed in sequences at various temperature points. The temperatures analyzed are T=115, 130, 145, 160, 180, 200, 250, 300, and 350° C. Goal is the comparison of the light-off determinations relative to the standard.

5. Standard Catalyst

The standard catalysts used as a benchmark is a DOC-FS7-4 with a metal loading of 2.6% Pd, 1.4% Pt, 3.1% BaO/Al2O3 (1:1 molar Pt:Pd)), with a notebook number of 640989-2-17-4SC. The standard was aged at various temperatures (650, 750, 850, 900° C.) to compare performance.

What is claimed is:

1. A metal oxide support material comprising nanoscaled iron-platinum group metal particles having a particle size from 0.5 to 10 nm, wherein at least 70% of the nanoscaled iron-platinum group metal particles are located on an outside surface layer of the metal oxide support material, and wherein the outside surface layer has an average volume of less than 50% based on the total volume of the metal oxide support material.

2. The metal oxide support material of claim 1, wherein the metal oxide support material is alumina, optionally doped with ceria and/or zirconia.

3. The metal oxide support material of claim 2, wherein the iron-platinum group metal particle is a combination of platinum and palladium or a combination of platinum, palladium and rhodium.

4. The metal oxide support material of claim 2, wherein the particle size of the iron-platinum group metal particles is from 0.5 to 4 nm.

5. The metal oxide support material of claim 2, wherein at least 80% of the nanoscaled iron-platinum group metal particles are located on the outside surface layer of the metal oxide support material, and wherein the outside surface layer has an average volume of 20% based on the total volume of the metal oxide support material.

6. The metal oxide support material claim 1, wherein the iron-platinum group metal particles are a combination of platinum and palladium or a combination of platinum, palladium and rhodium.

7. The metal oxide support material of claim 6, wherein the particle size of the iron-platinum group metal particles is from 0.5 to 4 nm.

8. The metal oxide support material of claim 6, wherein at least 80% of the nanoscaled iron-platinum group metal particles are located on the outside surface layer of the metal oxide support material, and wherein the outside surface layer has an average volume of 20% based on the total volume of the metal oxide support material.

9. The metal oxide support material of claim 1, wherein the particle size of the iron-platinum group metal particles is from 0.5 to 4 nm.

10. The metal oxide support material of claim 9, wherein at least 80% of the nanoscaled iron-platinum group metal particles are located on the outside surface layer of the metal oxide support material, and wherein the outside surface layer has an average volume of 20% based on the total volume of the metal oxide support material.

11. The metal oxide support material of claim 1, wherein at least 80% of the nanoscaled iron-platinum group metal particles are located on the outside surface layer of the metal oxide support material, and wherein the outside surface layer has an average volume of 20% based on the total volume of the metal oxide support material.

12. A process for the preparation of a metal oxide support material comprising a nanoscaled iron-platinum group metal, the process comprising:
    (i) dissolving a precursor of the iron-platinum group metal and a polymer in water and/or an organic solvent,
    (ii) reducing the precursor of the iron-platinum group metal, optionally adding a reducing reagent, and
    (iii) combining the solution obtained in (ii) with a metal oxide support material
    wherein the polymer is selected from derivatized polyethyleneimines or polyvinylamines, linear or cross linked homo- and/or copolymers of vinyl lactams, vinylimidazoles, vinylacetates, or vinyl formamides, linear or cross linked graft-homo and/or graft-copolymers of vinyl lactams, vinylimidazoles, vinylacetates, or vinyl formamides on polyether; and
    wherein the precursor is selected from the group consisting of a salt of hydroxides, oxides, phosphates, sulfates, sulfites, phosphonites, nitrites, borates, aluminates, silicates, cyanides, isocyanates, thioisocyanates, perchlorates, periodates, perbromates, chlorates, iodates, bromates, hypochlorites, acetylacetonates, acetates, or amine complexes.

13. The process of claim 12, wherein the precursor of the iron-platinum group metal particles is an iron-platinum metal salt selected from the group consisting of hydroxides, oxides or as amine complexes or as acetylacetonates or acetates.

14. A method of hydrogenating, dehydrogenating, oxidizing, metathesizing, and/or dealkylating, the method comprising using the metal oxide support material comprising nanoscaled metal particles according to claim 1 as a catalyst.

15. A diesel oxidation catalyst for the treatment of exhaust gas emissions from a diesel engine, wherein the metal oxide support material comprising nanoscaled iron-platinum group metal particles according to claim 1 is disposed on a carrier substrate.

16. A method for treating diesel engine exhaust gas stream emissions, the method comprising: contracting the exhaust stream with the diesel oxidation catalyst according to claim 15.

17. A process for the preparation of a metal oxide support material comprising a nanoscaled iron-platinum group metal, the process comprising:
  (i) dissolving a precursor of the iron-platinum group metal and a polymer in water and/or an organic solvent containing the metal oxide support material, and
  (ii) reducing the solution of (i)
  wherein the polymer is selected from derivatized polyethyleneimines or polyvinylamines, linear or cross linked homo- and/or copolymers of vinyl lactams, vinylimidazoles, vinylacetates, or vinyl formamides, linear or cross linked graft-homo and/or graft-copolymers of vinyl lactams, vinylimidazoles, vinylacetates, or vinyl formamides on polyether; and
  wherein the precursor is selected from the group consisting of a salt of hydroxides, oxides, phosphates, sulfates, sulfites, phosphonites, nitrites, borates, aluminates, silicates, cyanides, isocyanates, thioisocyanates, perchlorates, priodates, perbromates, chlorates, iodates, bromates, hypochlorites, acetylacetonates, acetates, or amine complexes.

18. The process of claim 17, wherein the precursor of the iron-platinum group metal is an iron-platinum group metal salt selected from the group consisting of hydroxides, oxides or as amine complexes or as acetylacetonates or acetates.

\* \* \* \* \*